USOO6356784B1

(12) United States Patent
Lozano et al.

(10) Patent No.: US 6,356,784 B1
(45) Date of Patent: Mar. 12, 2002

(54) METHOD OF TREATING MOVEMENT DISORDERS BY ELECTRICAL STIMULATION AND/OR DRUG INFUSION OF THE PENDUNULOPONTINE NUCLEUS

(75) Inventors: Andres M. Lozano, Toronto (CA); Mark T. Rise, Monticello, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/303,146

(22) Filed: Apr. 30, 1999

(51) Int. Cl.[7] .................................................. A61N 1/00
(52) U.S. Cl. .............................. 607/2; 604/522; 604/22
(58) Field of Search .......................... 604/21, 500, 503, 604/22, 522; 607/115, 116, 118, 139, 2, 3, 45

(56) References Cited

U.S. PATENT DOCUMENTS

| | | | | |
|---|---|---|---|---|
| 4,702,254 A | 10/1987 | Zabara | ........................ | 128/421 |
| 4,867,164 A | 9/1989 | Zabara | ........................ | 128/421 |
| 5,052,807 A | 10/1991 | Juday | ........................... | 356/375 |
| 5,293,879 A | 3/1994 | Vonk et al. | ................... | 128/782 |
| 5,711,316 A | 1/1998 | Elsberry et al. | ............. | 128/898 |
| 5,716,377 A | 2/1998 | Rise et al. | ...................... | 607/2 |
| 5,782,798 A | * 7/1998 | Rise | | |
| 5,832,932 A | 11/1998 | Elsberry et al. | ............. | 128/898 |

OTHER PUBLICATIONS

"The pedunculopontine nucleus in Parkinson's disease, progressive Supranuclear Palsy and Alzheimer's Disease" J Neurol Neurosurg Psychiatry Apr. 1998; 51(4): 540–3 (Abstract).*

"Neuronal loss in the pedunculopontine tegmental nucleus in Parkinson Disease and in Progressive Supranuclear Palsy" Hirsch El et al., Proc Natl Acad Sci USA Aug. 1987; 84(16): 5976–80 (Abstract).*

"Delayed emergence of a Parkinsonian Disorder in 38% of 29 older men Initially Diagnosed with Ideopathic rapid eye movement sleep behavior disorder" Schenck, Neurology Feb. 1996; 46(2): 388–93.*

"Neural Mechanism in Disorders of Movement", Crossman AR, Comp Biochem Physiol A 1989; 93(1): 141–9 (Abstract).*

(List continued on next page.)

*Primary Examiner*—Mark Bockelman
(74) *Attorney, Agent, or Firm*—Banner & Witcoff, Ltd.

(57) ABSTRACT

The present invention discloses techniques for treating movement disorders by electrical stimulation and/or drug infusion. The present invention utilizes an implantable signal generator and an electrode and/or an implantable pump and catheter. High electrical stimulation pulses and/or drug therapy is provided to the Pedunculopontine Nucleus (PPN). A sensor may be used to detect various symptoms of the movement disorders. A microprocessor algorithm may then analyze the output from the sensor to regulate the stimulation and/or drug therapy delivered to the PPN.

21 Claims, 11 Drawing Sheets-

OTHER PUBLICATIONS

"Neural Mechanisms for the clinical syndromes of Parkinson's Disease", Kato,M, Nippon Rinsho 1997 (Abstract).*

"The role of descending basal ganglia connections to the brain stem in Parkinsonian Akinesia" Aziz, TZ et al., Br J Neurosurg Jun. 1998; 12(3): 245–9 (Abstract).*

"The pedunculopontine nucleus in Parkinson's Disease" Rm Zweig et al., Ann Neurol Jul. 1989; 26(1): 41–6 (Abstract).*

"Pedunculopontine tegmental nucleus–induced inhibition of Muscle activity in the rat" MD Kelland et al., Behav Brain Res Sep.1989; 34(3): 213–34 (Abstract).*

"Muscle tone suppression and stepping produced by stimulation of Midbrain and Rostral Pontine Reticular formation" J. Neurosci Aug. 1990; 10(8): 2727–34 (Abstract).*

C.G. van Horne, "Multichannel semiconductor–based electrodes for in vivo electrochemical and electrophysiological studies in rat CNS", *Neuroscince Letter*, 130 (1990) 249–252.

Jordan LM, "Initiation of locomotion in mammals", *Ann Ny ACAD Sci* (Nov. 16, 1998) 860: 83–93.

Masdeu JC, "Astasia and gait failure with damage of the pontomesencephalic locomotor region", *Ann Neurol*, (May 1994)35(5):619–21.

Skinner RD, "Locomotor projections from the pedunculopontine nucleus to the medioventral medulla", *Neuroreport*, (Nov–Dec. 1990) 1(2–4):207–10.

Conde H, "The role of the pedunculopontine tegmental nucleus in relation to conditioned motor performance in the cat. II.Effect of reversible inactivation by intracerebral microinjections", *Exp Brain Res*, (Aug. 1998) 121(4):411–8.

Mathur A, "Locomotion and stereotype induced by scopolamine: contributions of muscarinic receptors near the pedunculopontine tegmental nucleus", *Brain Res*, (Nov. 1997) 14;775(1–2) 144–55.

Miwa H, "Injection of a GABA antagonist into the mesopontine reticular formation abolishes haloperidol–induced catalepsy in rats", *Neuroreport* (Nov. 1996) 4;7(15–17) 2475–8.

Rye DB, "Contributions of the pedunculopontine region to normal and altered REM sleep", *Sleep* (Sep. 1997) 20(9) 757–88.

Reese NB, "The pedunculopontine nucleus—auditory input, arousal and pathophysiology", *Prog Neurobiol* (Oct. 1995) 47(2) 105–33.

Yeomans JS "Role of tegmental cholinergic neurons in dopaminergic activation, antimuscarinic psychosis and schizophrenia" *Neuropsychopharmacoloby*, (Feb. 1995) 12(1)3–16.

* cited by examiner

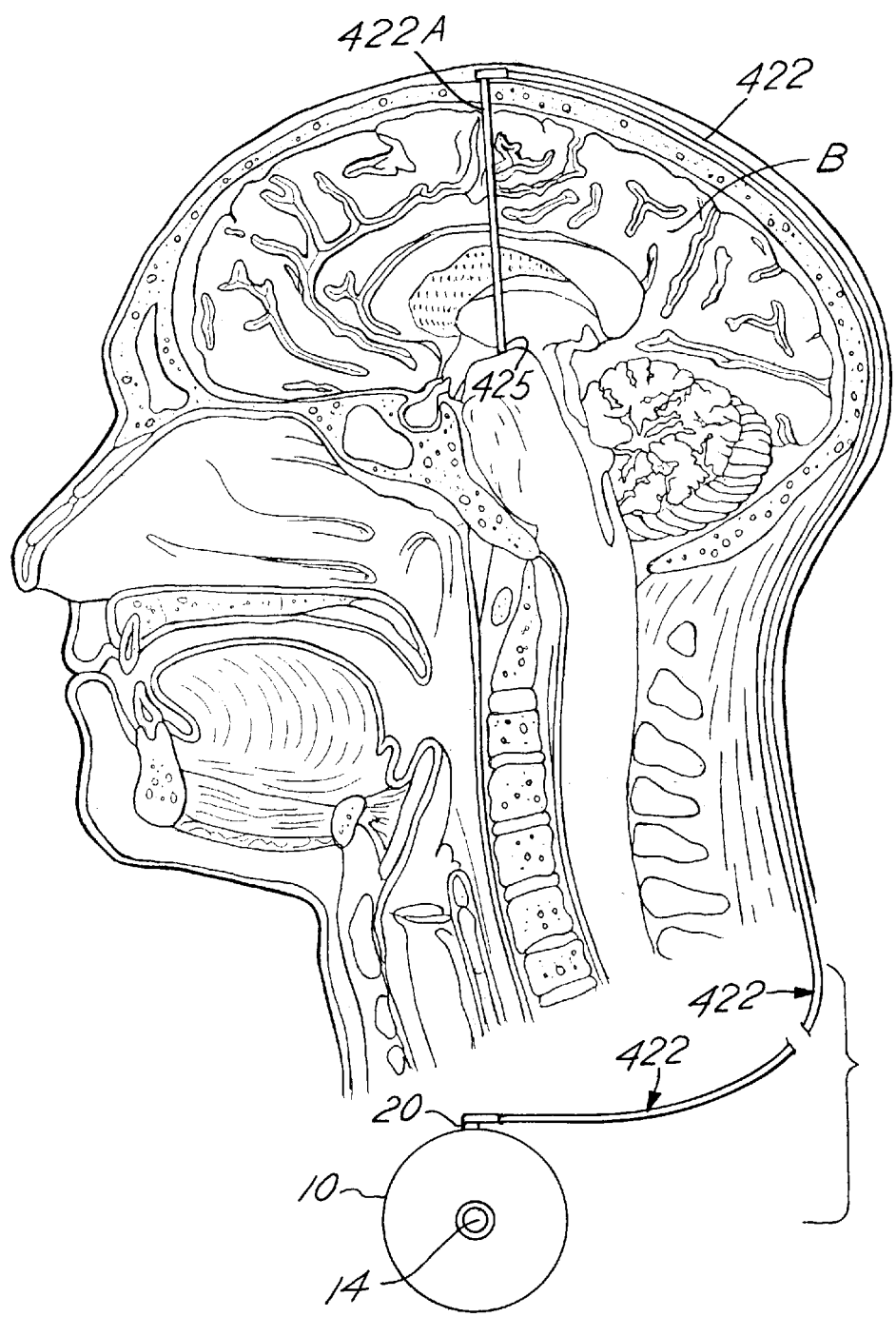

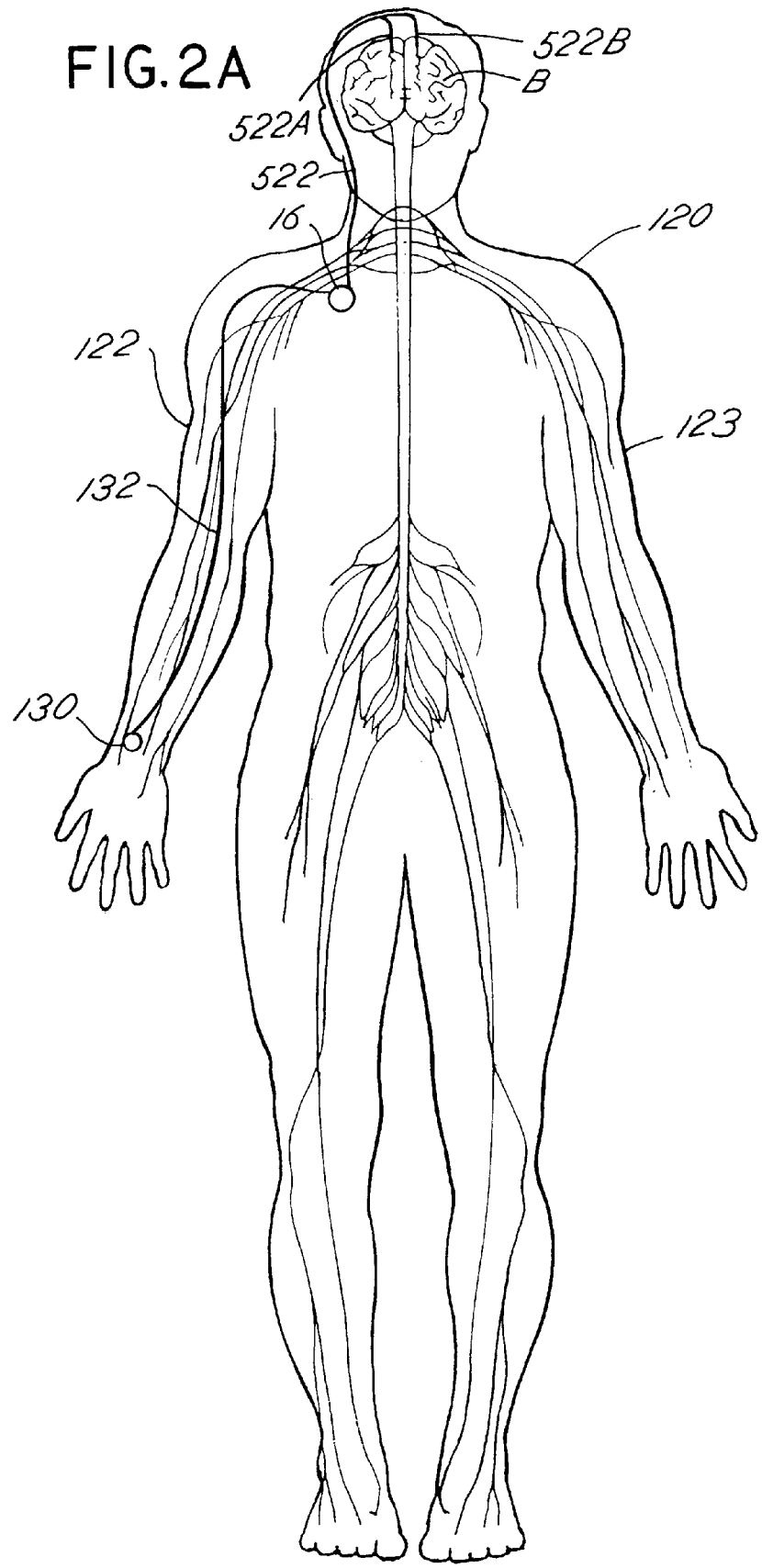

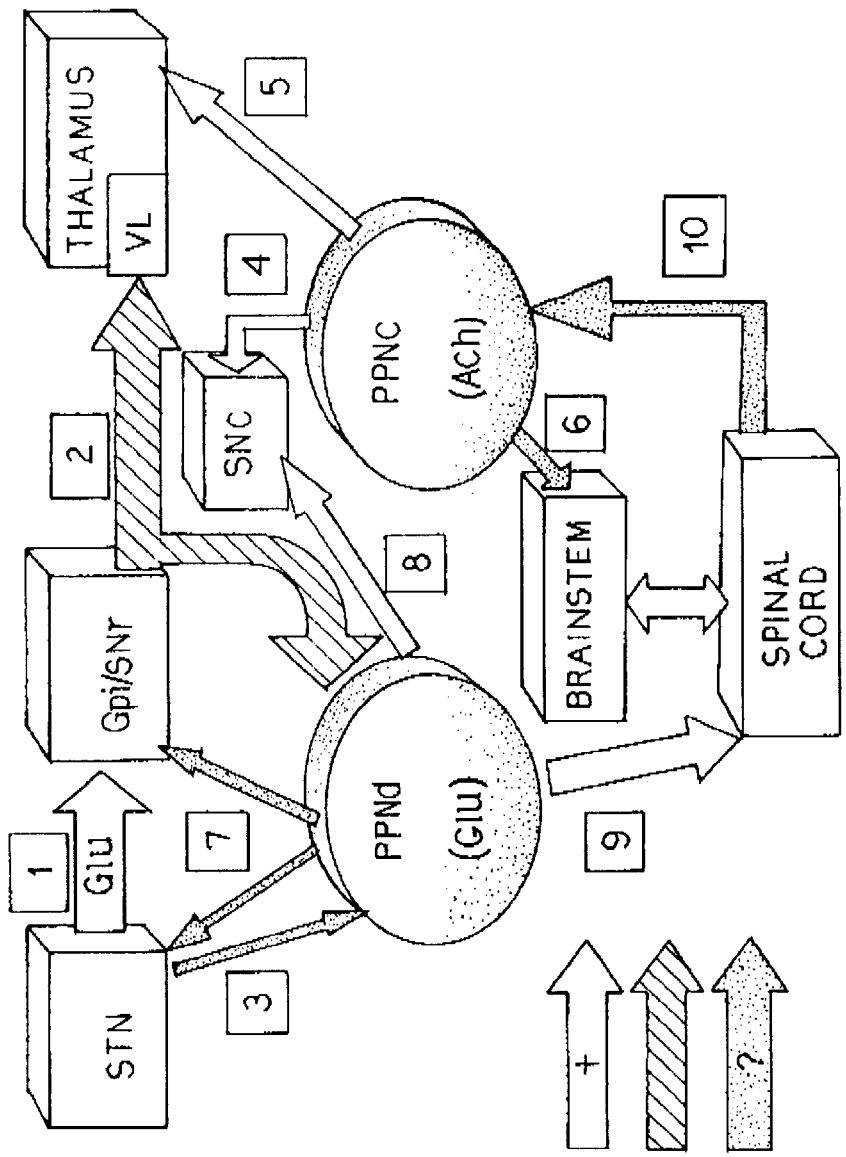

METHOD OF TREATING MOVEMENT DISORDERS BY ELECTRICAL STIMULATION AND/OR DRUG INFUSION OF THE PENDUNULOPONTINE NUCLEUS

BACKGROUND OF THE INVENTION

1. Field of the Invention

This invention relates to neural tissue stimulation and infusion techniques, and more particularly relates to such techniques for treating movement disorders by stimulation of and/or drug infusion into the pedunculopontine nucleus (PPN).

2. Description of Related Art

Patients with neurodegenerative diseases or trauma like cerebral infarct or spinal cord injury can have a variety of movement and muscle control problems, like resting, postural, intention or action tremor; dystonia (improper muscle tone); spasticity (undesirable movements, or muscle co-contraction); dyskinesia (poorly executed movements) or involuntary movements like ballismus, choreiform movements and torticollis (inappropriate movements or limb control). Many of these problems can be called hyperkinesia. Although they can be chronic, or worse, progressive, they also may have times of relative remission. Such problems are found, at certain stages, for patients with Parkinson's disease, multiple sclerosis, cerebral palsy, secondary to deafferentation pain, post stroke, post apoplexy or anoxia, post head or spinal trauma, post poisoning, cerebellar disease, etc. Dyskinesia also may result from long term usage of levodopa or other drugs, especially for Parkinson's patients.

A number of techniques are used for treating these and other movement disorders. Electrical stimulation and drug infusion techniques have become increasingly popular. In the case of electrical stimulation, an electrical lead having one or more electrodes is typically implanted near a specific site in the brain or spinal cord of a patient. The lead is coupled to a signal generator which delivers electrical energy through the electrodes to nearby neurons and neural tissue. The electrical energy delivered through the electrodes creates an electrical field causing excitation or inhibition of the nearby neurons. For example, stimulation of the vagus nerve as described in U.S. Pat. Nos. 4,702,254; 4,867,164; and 5,025,807 has been used to reduce the likelihood that a person with epilepsy will experience a seizure. For example, U.S. Pat. No. 5,716,377 entitled "Method of Treating Movement Disorders By Brain Stimulation" discloses techniques for stimulation of various portions of the brain.

These techniques, however, may not be as effective in the treatment of certain movement disorders such as akinesia and gait disorders for certain patients, and balance and walking disorders and many other symptoms that are resistant or are inadequately treated by current techniques. In addition, side effects of these therapies may limit the application of these techniques, for example, due to cognitive side effects, visual disturbances, speech disturbances and depression associated with these therapies. Further, these techniques may lose their effectiveness over time, sometimes due to degeneration of neurons, such that the patient may no longer respond to the treatment therapy in the certain portions of the brain, such as the thalamus, the globus pallidus, or the subthalamic nucleus. Other times, the treatment therapy may not be as effective to adequately alleviate a symptom of a movement disorder. Accordingly, there remains a need in the art to provide a treatment technique that directly targets neural tissue that handles motor control.

SUMMARY OF THE INVENTION

A preferred form of the invention uses electrical stimulation of the PPN to treat a movement disorder. The treatment is carried out by an implantable signal generator and an implantable electrode having a proximal end coupled to the signal generator and having a stimulation portion for electrically stimulating a predetermined stimulation site in the neural tissue. Alternatively, the treatment may be carried out by an implantable pump and a catheter having a proximal end coupled to the pump and having a discharge portion for infusing therapeutic dosages of the one or more drugs into a predetermined infusion site in neural tissue. By using the foregoing techniques, the symptoms of movement disorders, such as Parkinson's disease, Akinesia, Bradykinesia or Rigidity, Ballism, Hemiballism, Chorea, Torticollis, Spasticity or Dystonia can be alleviated. In addition to stimulation of the PPN, other portions of the brain or spinal cord may be stimulated to provide more comprehensive treatment therapy. In other embodiments of the invention, drug infusion may be used as treatment therapy instead of or in addition to the electrical stimulation.

In another embodiment of the invention, a sensor is used in combination with the signal generator and stimulating electrodes to treat the movement disorder. In this form of the invention, the sensor generates a sensor signal related to activity resulting from the movement disorder. Control means responsive to the sensor signal regulate the signal generator and pump so that the neural disorder is treated.

By using the foregoing techniques, the symptoms of many movement disorders can be controlled to a degree unattainable by prior art methods or apparatus.

BRIEF DESCRIPTION OF THE DRAWINGS

These and other advantages and features of the invention will become apparent upon reading the following detailed description and referring to the accompanying drawings in which like numbers refer to like parts throughout and in which:

FIG. 2 is a diagrammatic illustration of a catheter implanted in a brain according to a preferred embodiment of the present invention;

FIG. 2A is a diagrammatic illustration of the present invention in accordance with a preferred embodiment;

FIG. 11 is a schematic diagram depicting the types of connections between the PPN and related structures within the brain and spinal tissue.

DESCRIPTION OF THE PREFERRED EMBODIMENTS

The present invention discloses techniques for delivering treatment therapy to the Pedunculopontine Nucleus (PPN).

The applicants have discovered that movement disorders can be treated or controlled through surgical manipulation of the PPN, either directly or indirectly through its descending basal ganglia influences. Accordingly, the present invention incorporates electrical stimulation and/or drug infusion techniques to directly or indirectly influence the PPN. One or more electrodes and/or catheters are implanted in the brain so that the stimulation or infusion portions lie within or in communication with predetermined portions of the brain. The electrical stimulation or drug therapy influences the PPN to achieve the desired result.

Figure 1:
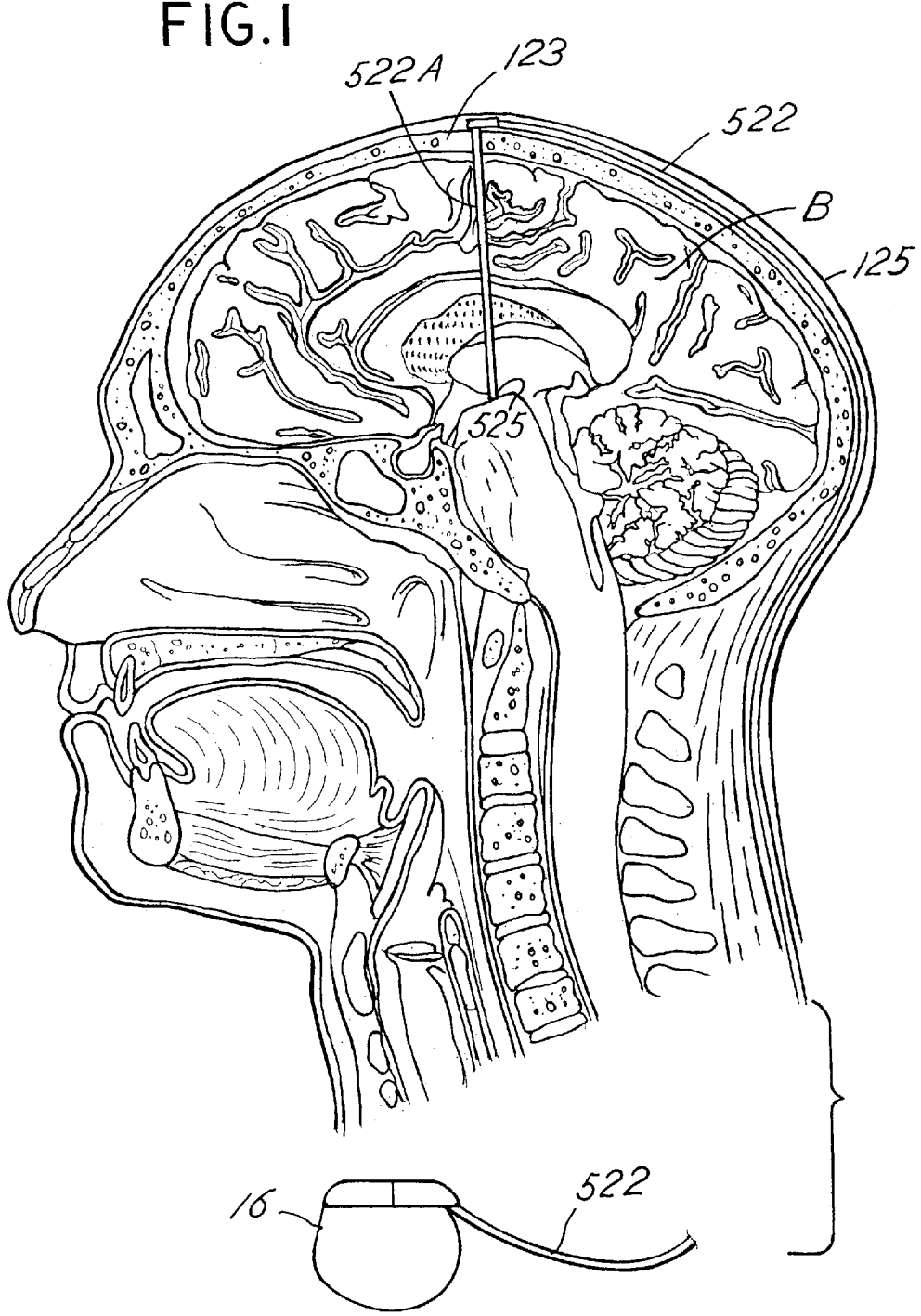
FIG. 1 is a diagrammatic illustration of an electrode implanted in a brain according to a preferred embodiment of the present invention and a signal generator coupled to the electrode.

Referring to FIG. 1, a system or device 16 made in accordance with the preferred embodiment may be implanted below the skin of a patient. A lead 522A is positioned to stimulate a specific site 525 in a brain (B). Device 16 may take the form of a modified signal generator Model 7424 manufactured by Medtronic, Inc. under the trademark Itrel II which is incorporated by reference. Lead 522A may take the form of any of the leads sold with the Model 7424 such as Model 3387, for stimulating the brain, and is coupled to device 16 by a conventional conductor 522.

The distal end of lead 522A terminates in four stimulation electrodes implanted into a portion of the brain by conventional stereotactic surgical techniques. However, other numbers of electrodes, such as two or six, may be used for various applications. Each of the four electrodes is individually connected to device 16 through lead 522A and conductor 522. Lead 522A is surgically implanted through a hole in the skull 123 and conductor 522 is implanted between the skull and the scalp 125 as shown in FIG. 1. Conductor 522 is joined to implanted device 16 in the manner shown. Referring to FIG. 2A, device 16 is implanted in a human body 120 in the location shown. Body 120 includes arms 122 and 123. Alternatively, device 16 may be implanted in the abdomen.

Conductor 522 may be divided into twin leads 522A and 522B that are implanted into the brain bilaterally as shown. Alternatively, lead 522B may be supplied with stimulating pulses from a separate conductor and signal generator. Leads 522A and 522B could be 1) two electrodes in two separate nuclei that potentiate each others effects or 2) nuclei with opposite effects with the stimulation being used to fine tune the response through opposing forces.

The targeted treatment site is either the PPN or a site that affects the neuronal circuitry as the PPN or a site that affects the same neuronal circuitry of the PPH. The PPN is the major brain stem motor area and is in a position to control muscle tone, rigidity, posture, balance, and locomotion. The PPN consists of a neurochemically and morphologically heterogeneous population of neurons. In the human brain, the PPN is bounded on its lateral side by fibers of the medial lemniscus and on its medial side by fibers of the superior cerebellar peduncle and its decussation. Rostrally, the anterior aspect of the PPN contacts the dorso-medial aspects of the posterolateral substantia nigra (SN), while the retrorubal field borders it dorsally. Caudally, the most dorsal aspect of the PPN is bounded by the cuneiform and subcuneiform nuclei and ventrally by the pontine reticular formation. The most caudal pole of the PPN is adjacent to neurons of the locus ceruleus. Typical stereotaxic coordinates for the PPN in a normal brain are as follows: (1) medial-lateral dimension 2 to 12 mm; dorsal-ventral dimension -6 to -18 mm; and anterior-posterior dimension -2 to -12 mm. (The medial-lateral dimensions are relative to midline of the brain; the anterior-posterior dimensions are relative to the midpoint between the anterior commissure and posterior commissure with negative indicating the posterior direction; the dorsal-ventral dimensions are relative to a line connecting the midpoints of the anterior and posterior commissures with negative being ventral to the line.)

The PPN generally consists of two subdivisions characterized by cell density. The pars compacta of the PPN (PPNc) is located within the caudal half of the nucleus in the dorsolateral aspect. Cells of the subnucleus pars dissipatus (PPNd) are distributed sparsely within the superior cerebellar peduncle and central tegmental tract. Cholinergic PPNc neurons are clustered along the dorsolateral border of the superior cerebellar peduncle (SP) at trochlear nucleus levels, whereas those in the PPNd are scattered along the SP from the midmesencephalic to midpontine levels. In the human brainstem, the cholinergic neuronal population of the PPN constitutes more than 90% of the neuronal population of the PPNc, whereas this percentage varies from 25% to 75% in the PPNd. A second prominent neuronal population contained within the PPNd is glutamatergic. Other neuronal types within the PPN may include doparninergic neurons, noradrenergic neurons, and GABA-ergic interneurons.

As shown in FIG. 11, certain relationship exists between the PPN and various structures of the basal ganglia. The PPNd, for example, provides excitatory glutamatergic outputs to many targets including the substantia nigra, the globus pallidus, the subthalamic nucleus and to brainstem centers and the spinal cord. Knowledge of these relationships may be utilized to provide treatment therapies for various disorders by targeting the PPN.

The stimulation administered by device 16 to the PPN depends on the specific movement disorder that is to be treated and the effect that the stimulation has on other parts of the brain. For example, PPNc neurons provide cholinergic inputs to the thalamus and SNc and receive important sensory feedback information from the spinal chord. Thus, stimulation to influence PPNc cholinergic neurons may be useful for modulation of steady-state locomotion. As another example, stimulation using a high frequency to block the output of the PPNc, thereby decreasing the excitatory input to the VL thalamus, would help treat hyperkinetic movement disorders. On the other hand, stimulation with a low frequency to facilitate the excitatory output of PPNc would alleviate symptoms for persons with hypokinetic movement disorders. Glutamatergic PPNd neurons receive outputs from the main subthalamic nucleus (STN), the internal globus pallidus (GPi), and the substantia nigra pars reticulata (SNr) and provide the main outflow of information to the spinal chord. Thus, stimulation to influence PPNd glutamatergic neurons may be useful for the control of initiation of locomotion. Further, the stimulation parameters may vary depending upon the type of neurons in the PPN that should be stimulated. To elicit locomotion, continuous mid-frequency stimulation on the order of 20–60 Hertz may be used. To reduce muscle tone, high frequency stimulation (greater than 100 Hertz) may be used.

The appropriate stimulation or drug delivery of the PPN in which lead 522A terminates, together with the effect of the treatment therapy on that portion of the brain for various disorders is provided in the following Table I.

| PPN Function | Clinical Problem | Strategy | Method | Predicted Outcome |
|---|---|---|---|---|
| Locomotion | 1. Insufficient or disrupted locomotor activity<br>2. Parkinson's disease,<br>3. Dystonia<br>4. Multiple system atrophy<br>5. Frontal lobe damage<br>6. Spasticity | Increase PPN activity | 1. Low freq activating stimulation<br>2. Deliver activating chemicals<br>3. Block inhibitory inputs with high freq. stimulation<br>4. Deliver blocking Chemicals | Improved posture, balance, gait |
| Sleep | 1. Insufficient sleep<br>2. Insomnia | Decrease PPN activity | 1. High freq blocking stimulation<br>2. Deliver blocking agents<br>3. Enhance inhibitory inputs with electrical stimulation<br>4. Deliver inhibitory chemicals | Improved ability to fall asleep and to maintain sleep |
| Sleep | 1. Excessive sleep<br>2. Cataplexy<br>3. Narcolepsy<br>4. Excessive daytime sleepiness | Increase PPN activity | 1. Low freq activating stimulation<br>2. Deliver activating chemicals<br>3. Block inhibitory inputs with high freq. stimulation<br>4. Deliver blocking chemicals | Improved Cataplexy, Narcolepsy, Increased wakefulness |
| Behavior | 1. Schizophrenia<br>2. Psychosis | Decrease PPN activity | 1. High freq blocking stimulation<br>2. Deliver blocking agents<br>3. Enhance inhibitory inputs with electrical stimulation<br>4. Deliver inhibitory chemicals | Control of schizophrenia symptoms, and of psychosis |
| Arousal | 1. Coma<br>2. Persistent vegetative states | Increase PPN activity | 1. Low freq activating stimulation<br>2. Deliver activating chemicals<br>3. Blocking inhibitory inputs with high freq. stimulation<br>4. Deliver blocking chemicals | Increased arousal |

As shown in this Table, the PPN activity can be either driven or blocked depending on the underlying disturbance. Whether the treatment therapy was driving or blocking would be determined by the choice of stimulation parameters or neural active agent delivered to the target. Any number of drugs may be administered including, but not limited to, an a nesthetic, a GABA agonist, a GABA antagonist, a glutamate antagonist, a glutamate agonist, a degrading enzyme, a reputake blocker, and a dopamine antagonist. An activating chemical may be used and includes any chemical that causes an increase in the discharge rate of the projection nerve cells from a region. An example (for projection neurons which receive glutamatergic excitation and GABA inhibition) would be an agonist of the transmitter substance glutamate (facilitating the excitation) or a GABA antagonist (blocking the inhibition). Conversely, a blocking chemical may be used and includes any chemical that inhibits the projection neurons thereby causing a decrease in the discharge rate of the projection nerve cells fr om a region. An example would be a glutamate antagonist (blocks excitatory input to the projection nerve cells) or a GABA agonist (enhances inhibition of the projection neurons). Referring back to FIG. 11, an example of an activating chemical for the PPNd is a GABA antagonist such as bicuculline and an example of a blocking agent would be a GABA agonist such as baclofen.

A combination of treatment therapies may be delivered to provide influencing of various neuronal types. For example, it may be desirable to concurrently influence the neurons in the PPNc and the PPNd to achieve an improved result. Increased local motor activity or improved posture and gait may be achieved by activating the PPN through stimulation or through the use of neuroactive substances. Alternatively, inhibiting the PPN through stimulation or the application of neuroactive substance may decrease the drive on the targets of the PPN including STN, GPi, SNR, SNpc, the thalamus, the brainstem and the spinal cord. Inhibition of the PPN could improve motor and locomotor function as well as protect susceptible neurons from the consequences of excitotoxic glutamate and acetylcholine induced injury originating from the PPN. In addition because of the important role of PPN and brainstem cholinergic systems in arousal in sleep and in psychiatric disturbances, modulation of the PPN could also be used in the treatment of such disorders as schizophrenia, narcolepsy, cataplexy, states of impaired arousal including coma and in a variety of other psychiatric disorders.

In addition to stimulation of the PPN, it may be desirable to stimulate concurrently other portions of the brain. For example, a combination of electrical stimulation of the PPN with a certain pattern in combination with direct stimulation of the subthalamic nucleus (STN) with another pattern may be utilized to achieve optimal motor planning and improvements in all of the cardinal signs and symptoms of Parkinson's disease (PD). Stimulation of the PPN may be used to initiate movement and thereafter known techniques for stimulation of other parts of the brain or spine may be used to continue the treatment therapy. A combination may be electrical stimulation and/or drug infusion (discussed herein) and may be implemented. Examples of known stimulation and infusion techniques in other parts of the brain or spinal cord for treating movement disorders include U.S. Pat. Nos. 5,716,377 and 5,711,316. These references are incorporated herein by reference in their entirety.

The embodiments of the present invention shown above are open-loop systems. The microcomputer algorithm programmed by the clinician sets the stimulation parameters of signal generator 16. This algorithm may change the parameter values over time but does so independent of any changes in symptoms the patient may be experiencing. Alternatively, a closed-loop system discussed below which incorporate a sensor 130 to provide feedback could be used to provide enhanced results. Sensor 130 can be used with a closed loop feedback system in order to automatically determine the level of electrical stimulation necessary to alleviate the symptoms of the movement disorder.

As illustrated in FIG. 2A, sensor 130 is attached to or implanted into a portion of a patient's body suitable for detecting symptoms of the movement disorder being treated, such as a motor response or motor behavior. Sensor 130 is adapted to sense an attribute of the symptom to be controlled or an important related symptom. For movement disorders that result in abnormal movement of an arm, such as arm 122, sensor 130 may be a motion detector implanted in arm 122 as shown. For example, sensor 130 may sense three-dimensional or two-dimensional motion (linear rotational or joint motion), such as by an accelerometer. One such sensor suitable for use with the present invention is described in U.S. Pat. No. 5,293,879 (Vonk). Another suitable accelerometer is found in pacemakers manufactured by Medtronic, Inc. and described in patent application Ser. No. 08/399072 filed Mar. 8, 1995, in the names of Jarnes Sikorski and Larry R. Larson and entitled "Package Integrated Accelerometer". Sensor 130 also may be placed in device 16 in order to detect abnormal movement resulting from the motion disorder being treated.

Sensor 130 also may be capable of detecting gravity direction or motion relative to some object (e.g., a magnet) either implanted or fixed nearby. Sensor 130 also may take the form of a device capable of detecting force in muscles or at joints, or pressure.

Sensor 130 may detect muscle EMG in one, two or more muscles, or in reciprocal muscles at one joint. For such detection, sensor 130 may take the form of a recording electrode inserted into the muscle of interest.

Yet another form of sensor 130 would include a device capable of detecting nerve compound action potentials (e.g., either sensory afferent information from muscle or skin receptors or efferent motor potentials controlling a muscle of interest).

For certain types of patients, sensor 130 may take the form of device detecting the posture of the patient.

Sensor 130 also may take the form of a device capable of detecting nerve cell body or axon activity that is related to the pathways at the cause of the symptom, or that reflects sensations which are elicited by the symptom. Such a sensor may be located deep in the brain. For such detecting, sensor 130 may take the form of an electrode inserted into the internal capsule of the brain, or other locations that are part of the basal ganglia. Brain EEG (e.g., motor cortex potentials recorded above the motor neurons controlling specific muscle groups) also may be detected by sensor 130. In this case, sensor 130 would take the form of an electrode with impedance values preferably chosen to optimize recording of electrical signals. Signals that are received by the sensor may by amplified before transmission to circuitry contained within device 16.

Sensor 130 may take the form of a transducer consisting of an electrode with an ion selective coating applied which is capable of directly transducing the amount of a particular transmitter substance or its breakdown by-products found in the interstitial space of a region of the brain such as the ventral lateral thalamus. The level of the interstitial transmitter substance is an indicator of the relative activity of the brain region. An example of this type of transducer is described in the paper "Multichannel semiconductor-based electrodes for in vivo electrochemical and electrophysiological studies in rat CNS" by Craig G. van Home, Spencer Bement, Barry J. Hoffer, and Greg A. Gerhardt, published in *Neuroscience Letters*, 120 (1990) 249–252.

For tremor, the relative motion of a joint or limb or muscle EMG may be productively sensed. Sensing electrical activity of neurons in various locations of the motor circuitry also is helpful. Recording the electrical activity in the thalamus or cerebellum will reveal a characteristic oscillating electrical activity when tremor is present. For Ballism, Hemiballism or tremor, sensor 130 may take the form of an accelerometer detecting relative motion of ajoint and limb or muscle EMG. For Dystonia, sensor 130 may take the form of a device for detecting relative motion of a joint or limb or muscle EMG.

Sensor 130 may be external to the body communicating with the implanted portions through telemetry.

Figure 3:
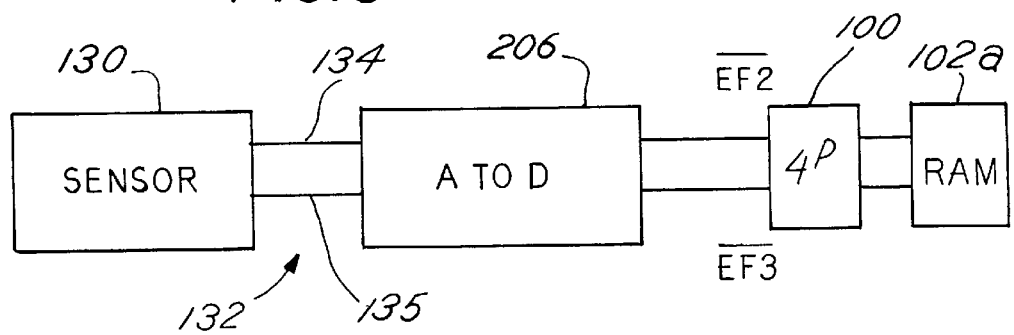
FIG. 3 is a schematic block diagram of a sensor and analog to digital converter circuit used in the preferred embodiment of the invention.
Figure 4:
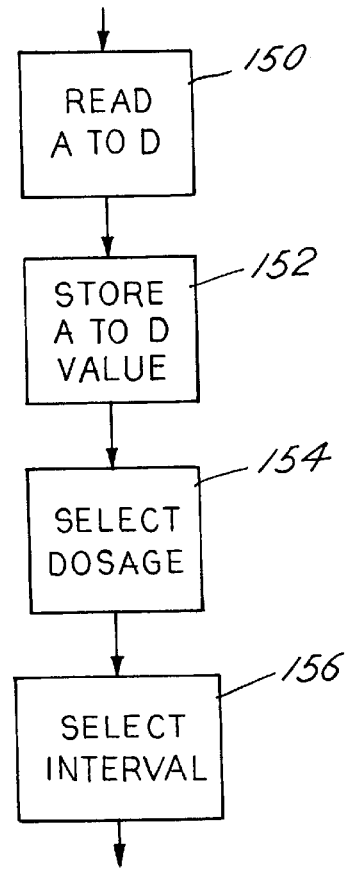
FIG. 4 is a flow chart illustrating a preferred form of a microprocessor program for utilizing the sensor to control drug dosage administered to the brain.

Referring to FIGS. 3 and 4, the output of sensor 130 is coupled by cable 132, comprising conductors 134 and 135, to the input of an analog to digital converter 206 within device 16. Alternatively, the output of an external sensor would communicate with the implanted pulse generator through a telemetry downlink.

Figure 5:
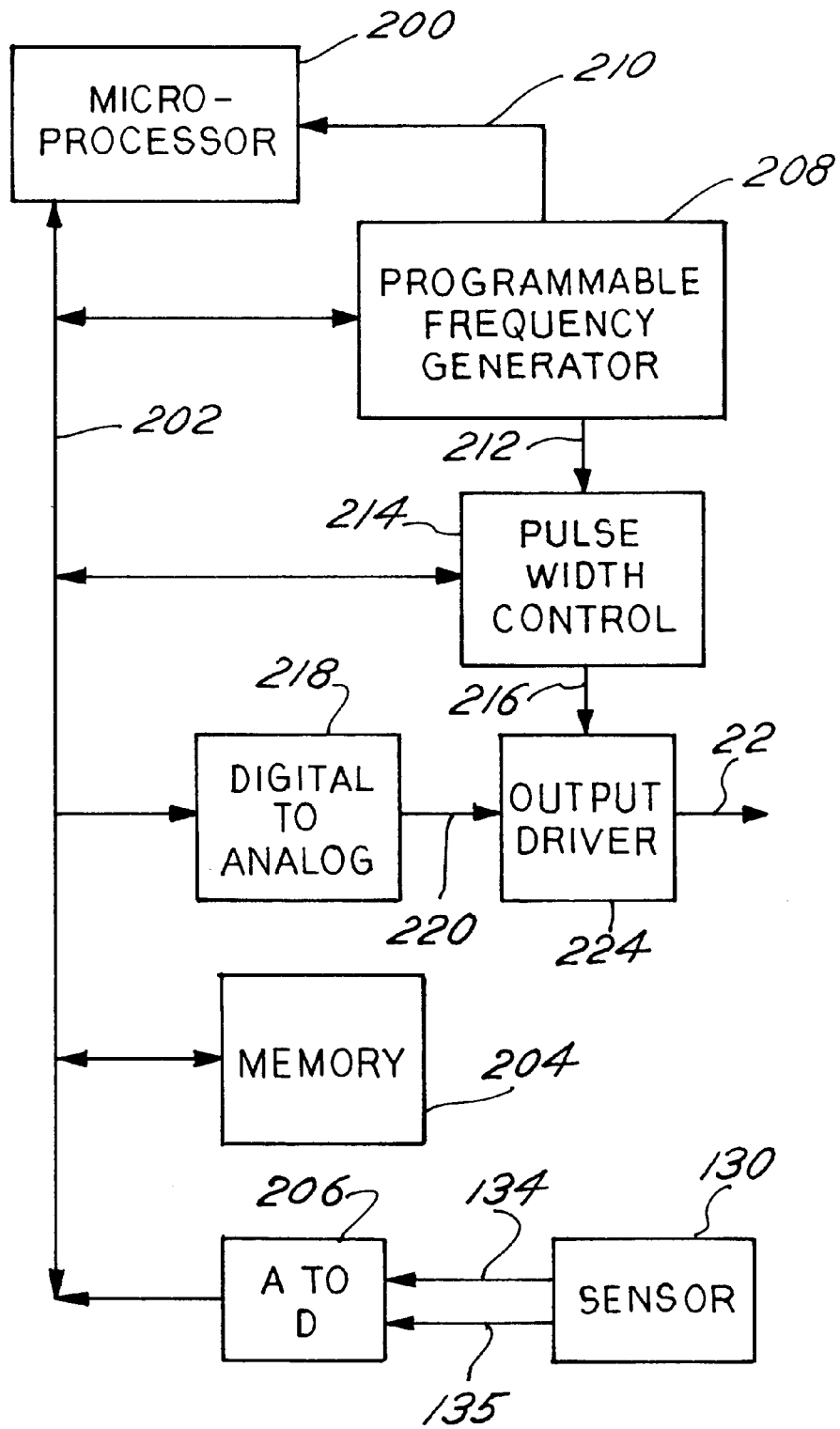
FIG. 5 is a schematic block diagram of a microprocessor and related circuitry for utilizing the sensor to control stimulation administered to the brain.
Figure 6:
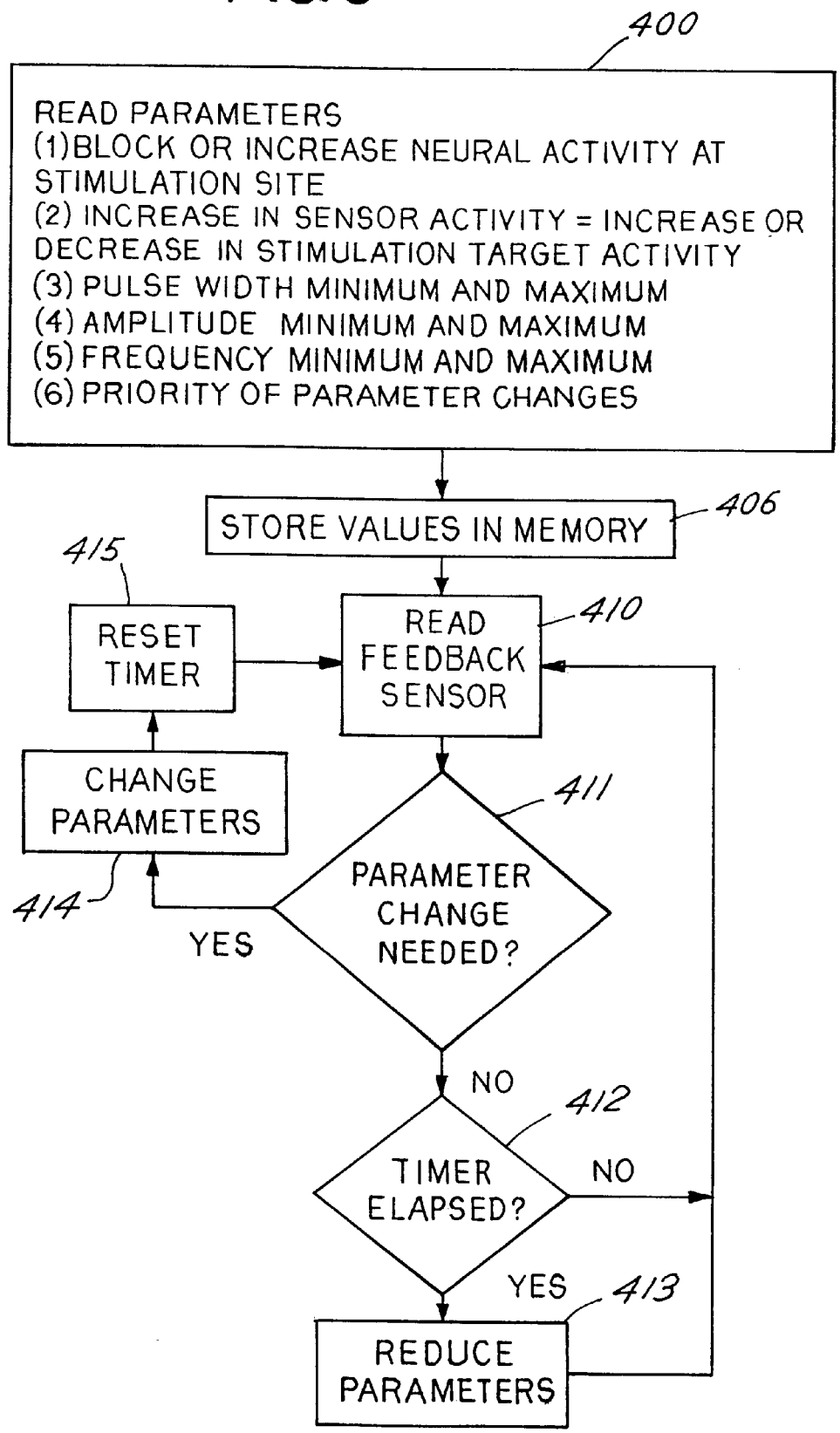
FIGS. 6–10 are flow charts illustrating a preferred form of microprocessor program for generating stimulation pulses to be administered to the brain.

The remainder of the components shown in FIG. 3 are included in device 16. Referring now to FIG. 5, the output of the analog to digital converter 206 is connected to a microprocessor 200 through a peripheral bus 202 including address, data and control lines. Microprocessor 200 processes the sensor data in different ways depending on the type of transducer in use. When the signal on sensor 130 exceeds a level programmed by the clinician and stored in a memory 204, increasing amounts of stimulation will be applied through an output driver 224.

Referring to FIG. 5, the stimulus pulse frequency is controlled by programming a value to a programmable frequency generator 208 using bus 202. The programmable frequency generator provides an interrupt signal to microprocessor 200 through an interrupt line 210 when each stimulus pulse is to be generated. The frequency generator may be implemented by model CDP1878 sold by Harris Corporation. The amplitude for each stimulus pulse is programmed to a digital to analog converter 218 using bus 202. The analog output is conveyed through a conductor 220 to an output driver circuit 224 to control stimulus amplitude.

Microprocessor 200 also programs a pulse width control module 214 using bus 202. The pulse width control provides an enabling pulse of duration equal to the pulse width via a conductor 216. Pulses with the selected characteristics are then delivered from device 16 through cable 522 and lead 522A to the PPN basal ganglia, thalamus or other region of the brain.

Microprocessor 200 executes an algorithm shown in FIGS. 6–10 in order to provide stimulation with closed loop feedback control. At the time the stimulation device 16 is implanted, the clinician programs certain key parameters into the memory of the implanted device via telemetry. These parameters may be updated subsequently as needed. Step 400 in FIG. 6 indicates the process of first choosing whether the neural activity at the stimulation site is to be blocked or facilitated (step 400(1)) and whether the sensor location is one for which an increase in the neural activity at that location is equivalent to an increase in neural activity at the stimulation target or vice versa (step 400(2)). Next the clinician must program the range of values for pulse width (step 400(3)), amplitude (step 400(4)) and frequency (step 400(5)) which device 16 may use to optimize the therapy. The clinician may also choose the order in which the parameter changes are made (step 400(6)). Alternatively, the clinician may elect to use default values.

Figure 7:
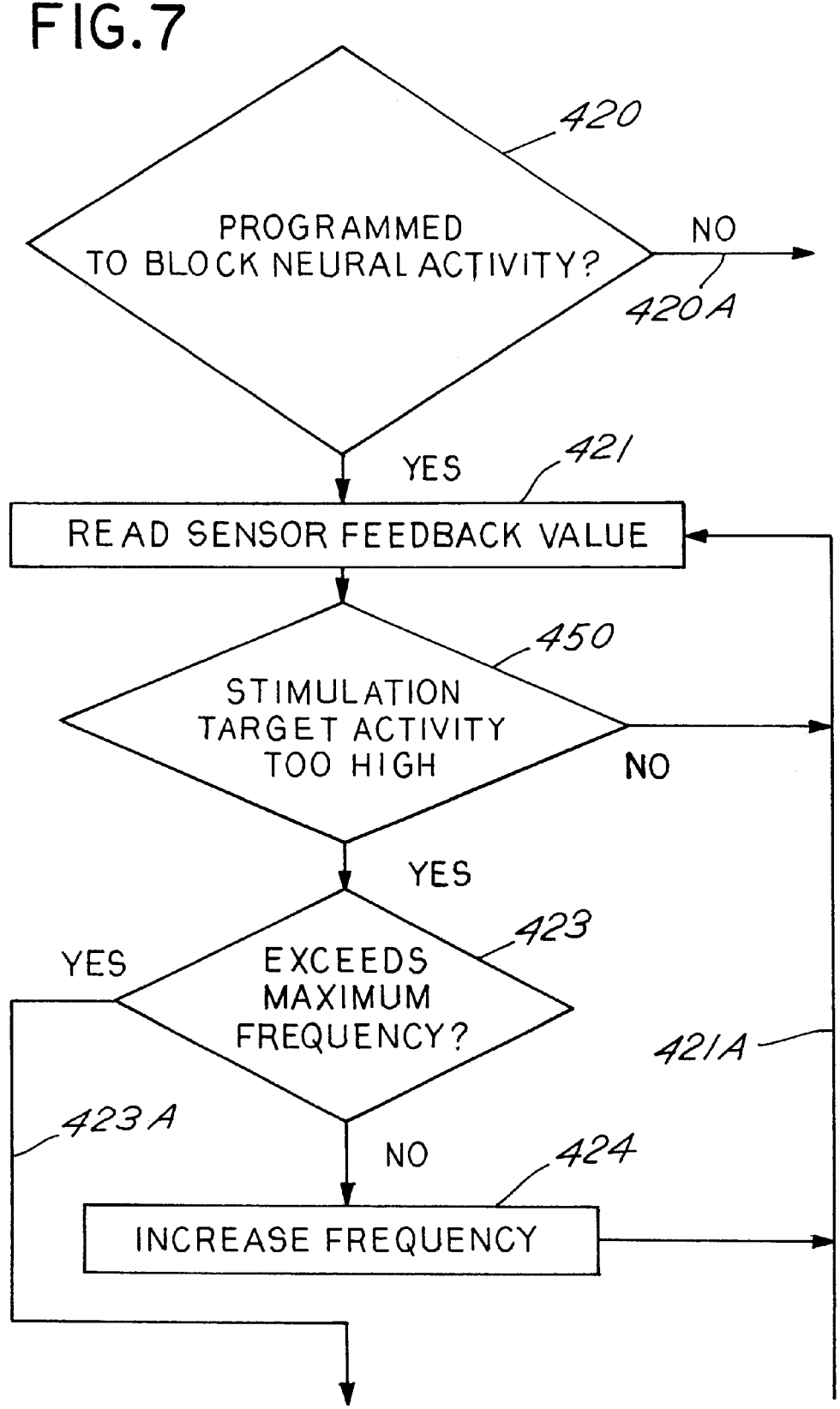

The algorithm for selecting parameters is different depending on whether the clinician has chosen to block the neural activity at the stimulation target or facilitate the neural activity. FIG. 7 details steps of the algorithm to make parameter changes.

Figure 8:
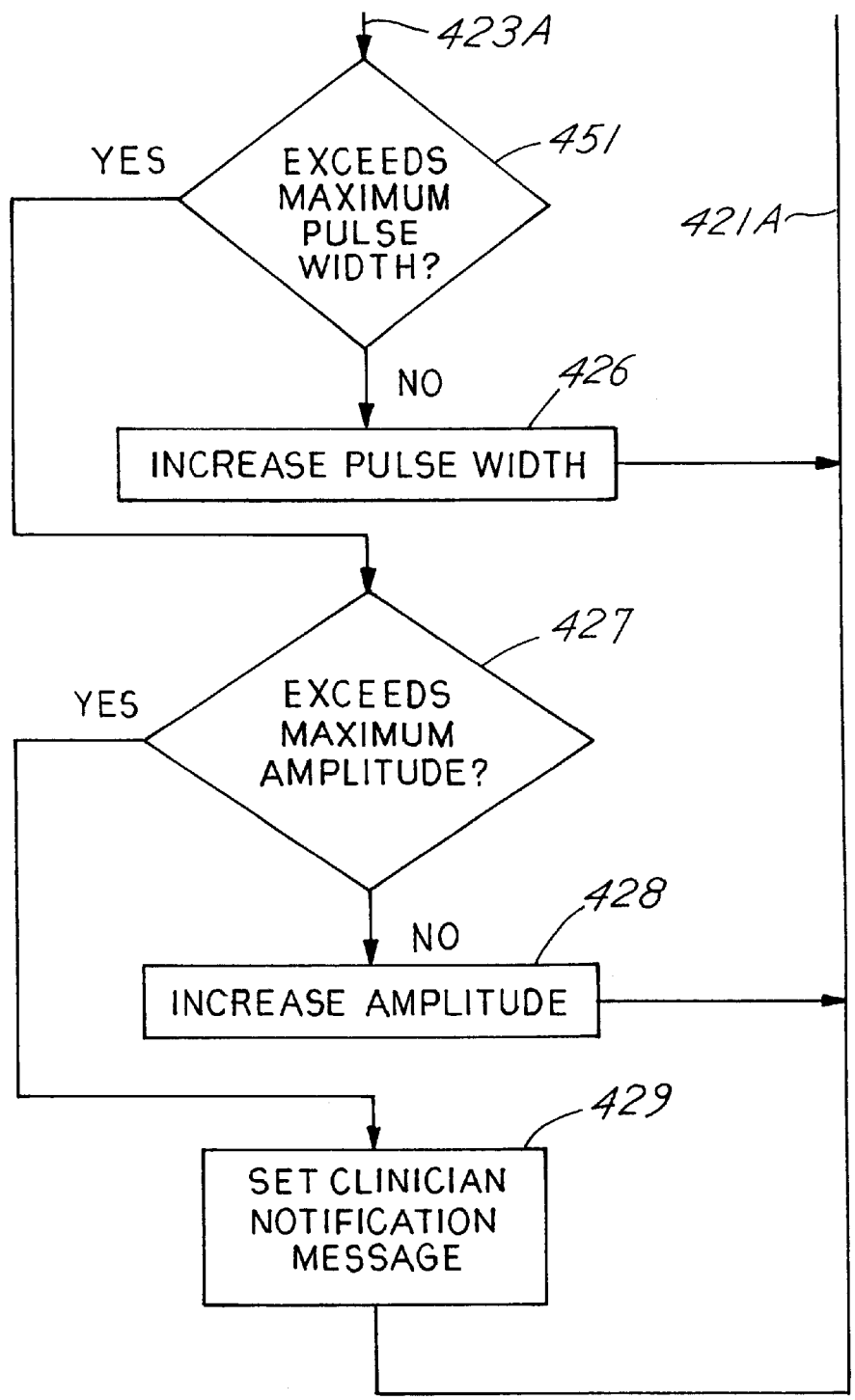
Figure 9:
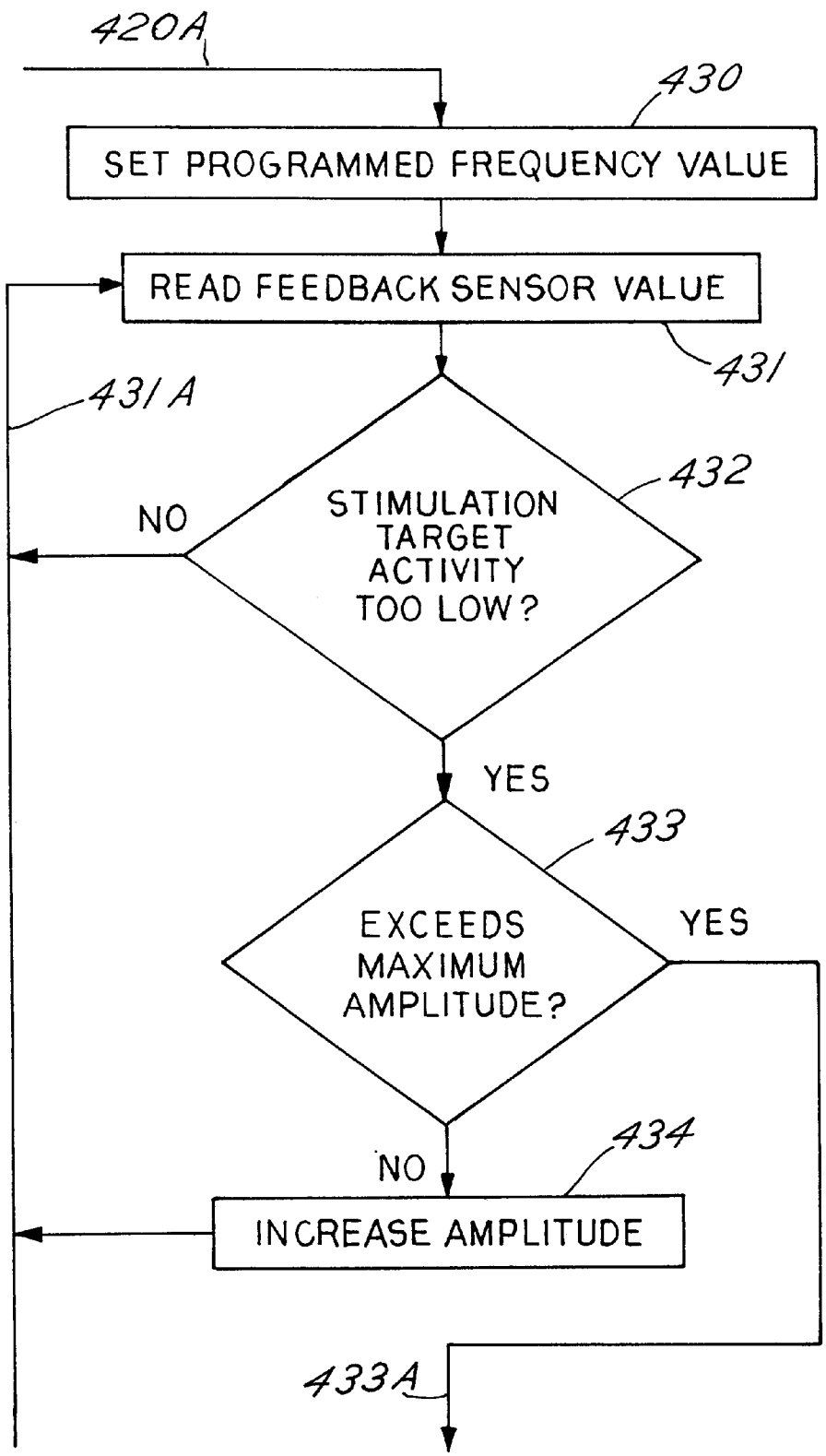

The algorithm uses the clinician programmed indication of whether the neurons at the particular location of the stimulating electrode are to be facilitated or blocked to decide which path of the parameter selection algorithm to follow (step 420, FIG. 8). If the neuronal activity is to be blocked, device 16 first reads the feedback sensor 130 in step 421. If the sensor values indicate the activity in the glutamatergic neurons is too high (step 422), the algorithm in this embodiment first increases the frequency of stimulation in step 424 provided this increase does not exceed the preset maximum value set by the physician. Step 423 checks for this condition. If the frequency parameter is not at the maximum, the algorithm returns to step 421 through path 421A to monitor the feed back signal from sensor 130. If the frequency parameter is at the maximum, the algorithm next increases the pulse width in step 426 (FIG. 9), again with the restriction that this parameter has not exceeded the maximum value as checked for in step 425 through path 423A. Not having reached maximum pulse width, the algorithm returns to step 421 to monitor the feedback signal from sensor 130. Should the maximum pulse width have been reached, the algorithm next increases amplitude in a like manner as shown in steps 427 and 428. In the event that all parameters reach the maximum, a notification message is set in step 429 to be sent by telemetry to the clinician indicating that device 16 is unable to reduce neural activity to the desired level.

Figure 10:
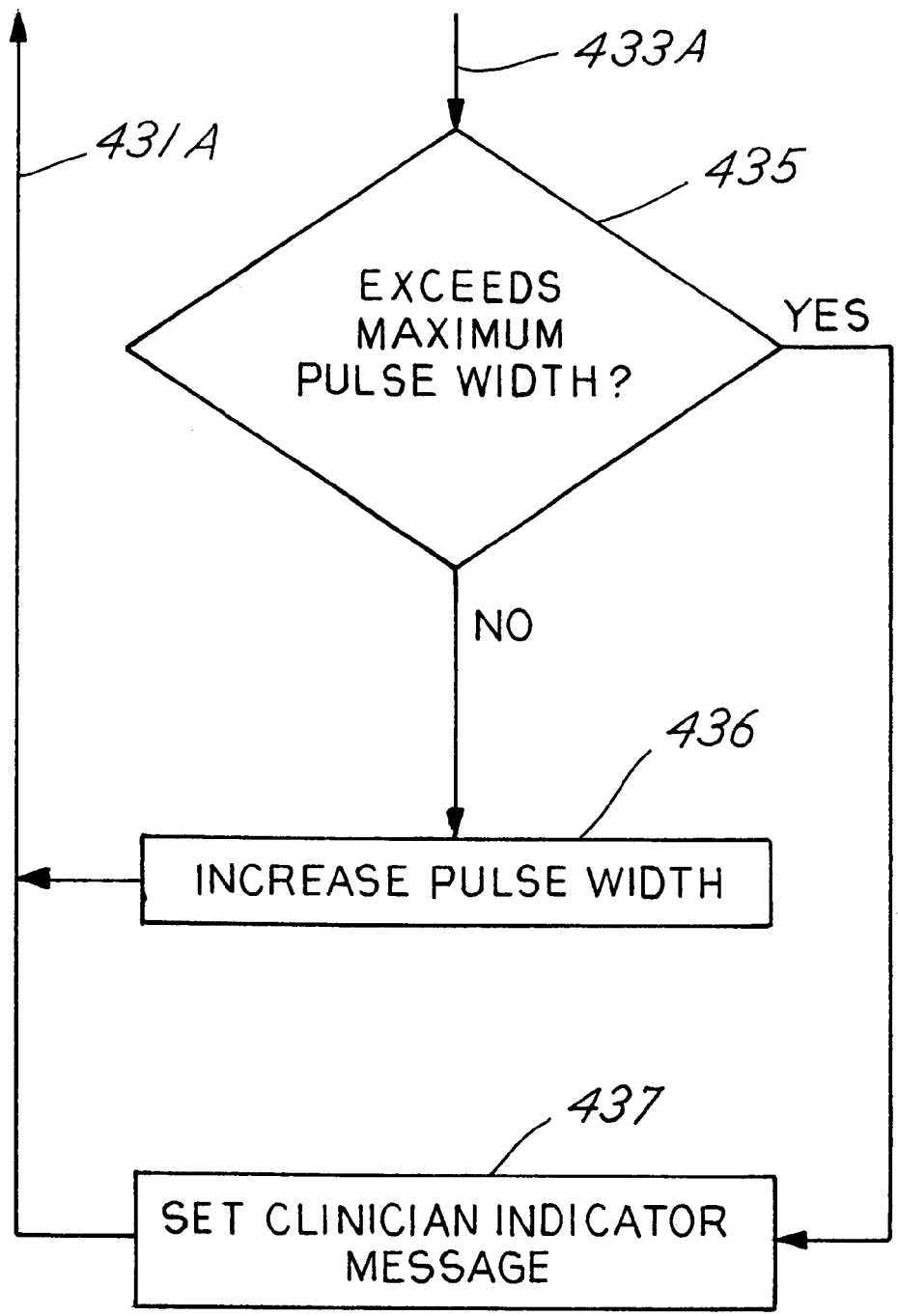

If, on the other hand, the stimulation electrode is placed in a location which the clinician would like to activate to achieve desired effect, the algorithm would follow a different sequence of events. In the preferred embodiment, the frequency parameter would be fixed at a value chosen by the clinician to facilitate neuronal activity in step 430 (FIG. 10) through path 420A. In steps 431 and 432 the algorithm uses the values of the feedback sensor to determine if neuronal activity is being adequately controlled. In this case, inadequate control indicates that the neuronal activity of the stimulation target is too low. Neuronal activity is increased by first increasing stimulation amplitude (step 434) provided it doesn't exceed the programmed maximum value checked for in step 433. When maximum amplitude is reached, the algorithm increases pulse width to its maximum value in steps 435 and 436 (FIG. 10). A lack of adequate control of the feedback parameters, even though maximum parameters are used, is indicated to the clinician in step 437. After steps 434, 436 and 437, the algorithm returns to step 431 through path 43 1A, and the feedback sensor again is read.

It is desirable to reduce parameter values to the minimum level needed to establish the appropriate level of neuronal activity in the subthalamic nucleus. Superimposed on the algorithm just described is an additional algorithm to readjust all the parameter levels downward as far as possible. In FIG. 4, steps 410 through 415 constitute the method to do this. When parameters are changed, a timer is reset in step 415. If there is no need to change any stimulus parameters before the timer has counted out, then it may be possible due to changes in neuronal activity to reduce the parameter values and still maintain appropriate levels of neuronal activity in the target neurons. At the end of the programmed time interval, device 16 tries reducing a parameter in step 413 to determine if control is maintained. If it is, the various parameter values will be ratcheted down until such time as the sensor values again indicate a need to increase them. While the algorithms in FIGS. 6–10 follow the order of parameter selection indicated, other sequences may be programmed by the clinician.

The present invention may be implemented by providing pulses to lead 522A having amplitudes of 0.1 to 20 volts, pulse widths varying from 0.02 to 1.5 milliseconds, and repetition rates varying from 2 to 2500 Hz. The appropriate stimulation pulses are generated by device 16 based on the computer algorithm shown in FIGS. 6–10 that read the output of converter 140 and makes the appropriate analysis.

For some types of movement disorders, a microprocessor and analog to digital converter will not be necessary. The output from sensor 130 can be filtered by an appropriate electronic filter in order to provide a control signal for device 16.

Microprocessor 200 within device 16 can be programmed so that the desired stimulation can be delivered to the PPN as described in Tables I and II. Alternatively, sensor 130 can be used with a closed loop feedback system in order to automatically determine the type of stimulation necessary to alleviate movement disorder symptoms.

Movement disorders may also be treated by infusion of one or more drugs into the PPN. Agonists or antagonists of any number of neurotransmitters may be used to affect the PPN including, but not limited to, acetylcholine, adenosine, GABA, glutamate, histamine, noradrenaline, opiates, and serotonin. All except glutamate and histamine are thought to be inhibitory. For example, excitatory amino acids or GABA agonists may be used to generally increase motor activity, while inhibitory GABAergic inputs may be used to inhibit locomotor activity. In general, glutamate agonists and antagonists may be used to influence the PPNc and the acetylcholine agonists and antagonists may be used to influence the PPNd. Excitatory amino acids or cholinergic agonists may be used to increase neural activity, while inhibitory GABAergic inputs may be used to inhibit neural activity. The effects of these manipulations on motor function relates to whether the normal or pathological role of the structure affected is to increase or decrease motor activity.

Advantageously under the present invention, the PPN may be influenced to control or treat various movement disorders including, but not limited to, Parkinson's disease, dystonia, myoclonus, chorea, akinesia, rigidity, tremor, gait abnormalities, postural disorder, motor complications, and neuropsychiatric complications. The PPN is the major stem motor area and is in a position to control muscle tone, rigidity, posture, balance, and locomotion. Stimulation of the PPN may improve or reverse postural and gait deficits to a greater extent than any of the currently used therapies. In addition, stimulation of the PPN may arrest and even reverse these disturbances in patients that are failing surgery and Deep Brain Stimulation (DBS) at other brain sites such as the thalamus, globus pallidus, and subthalamic nucleus.

As shown in the above table, PPN disfunction has also been implicated in schizophrenia, in sleep disturbances and in regulation of the state of arousal. Consequently, PPN manipulation either with stimulation or with the delivery of neuroactive substances may be used to treat psychiatric illness (including schizophrenia and depression), sleep disorders (including sleep disorders and narcolepsy and cataplexy) and altered states of arousal (including persistent vegetative states and coma). Other areas of potential therapeutic use by the present invention is in the treatment of anxiety disorders and depression.

Those skilled in that art will recognize that the preferred embodiments may be altered or amended without departing from the true spirit and scope of the invention, as defined in the accompanying claims.

We claim:

1. A method for treating movement disorders by means of an implantable signal generator and a lead having a proximal end coupled to the signal generator and a distal portion having at least one electrode, the method comprising the steps of:

(a) implanting at least one electrode so that the stimulation portion lies at least in direct communication with tissue elements of a pedunculopontine nucleus (PPN);

(b) coupling the proximal end of the implanted electrode to the signal generator; and (c) operating the signal generator to stimulate the PPN.

2. A method, as claimed in claim 1, further comprising the steps of:

(d) sensing the extent of the movement disorder and generating a sensor signal; and (e) regulating the operation of the electrode in response to the sensor signal.

3. A method, as claimed in claim 2, wherein said step of regulating comprises the step of executing a control algorithm.

4. A method, as claimed in claim 3, wherein said step of generating a sensor signal includes the steps of detecting a symptom of the movement disorder and communicating with the control algorithm by telemetry.

5. A method, as claimed in claim 2, wherein the step of sensing includes the step of sensing a physiological symptom of the movement disorder.

6. A method, as claimed in claim 2, wherein the step of sensing includes the step of sensing a chemical symptom of the movement disorder.

7. A method, as claimed in claim 2, wherein the step of regulating includes the step of adjusting at least one parameter of the stimulation, the parameter being selected from the group consisting of amplitude, pulse width and frequency.

8. A method, as claimed in claim 7, further comprising the step of:

(f) adjusting at least one parameter of the stimulation downward to decrease the effects of the stimulation.

9. A method, as claimed in claim 1, wherein the step of operating includes the step of selecting amplitude, width and frequency of stimulation by the electrode.

10. A method, as claimed in claim 1, wherein said step of operating includes the step of operating the signal generator to provide a burst of electrical energy to initiate movement.

11. A method, as claimed in claim 1, wherein said step of operating includes the step of operating the signal generator to pulse at a repetition rate of 2–2500 Hertz.

12. A method, as claimed in claim 1, wherein the step of operating includes the step of operating the signal generator to pulse at a repetition rate of 10–2500 Hertz.

13. A method, as claimed in claim 1, further comprising the steps of:

(d) implanting at least one secondary electrode so that a secondary stimulation portion lies in communication with a predetermined portion of a brain;

(e) coupling the secondary electrode to the signal generator; and (f) operating the signal generator to stimulate the brain.

14. A method, as claimed in claim 1, further comprising the steps of:

(d) implanting at least one catheter so that a secondary stimulation portion lies in communication with a predetermined portion of a brain;

(e) coupling the catheter to a pump; and (f) operating the pump to deliver drug to the brain.

15. A therapeutic treatment method for treating movement disorders by means of an implantable pump and a catheter having a proximal end coupled to the pump and a discharge portion for infusing therapeutic dosages of at least one drug, the method comprising the steps of:

(a) implanting the catheter so that the discharge portion lies in at least direct communication with tissue element of a pedunculopontine nucleus (PPN);

(b) coupling the catheter to the pump; and (c) operating the pump to deliver the drug to the PPN.

16. A method, as claimed in claim 15, wherein the step of operating includes the step of delivering to the PPN at least one drug selected from the group consisting of an anesthetic, a GABA agonist, a GABA antagonist, a glutamate antagonist, a glutamate agonist, a degrading enzyme, a reputake blocker, and a dopamine antagonist.

17. A method, as claimed in claim 16, wherein the step of operating includes the step of selecting a time interval for drug delivery.

18. A method, as claimed in claim 15, wherein the step of operating includes the step of selecting a drug dosage.

19. A method, as claimed in claim 15, further comprising the steps of:

(d) sensing the extent of the movement disorder and generating a sensor signal; and (e) regulating the operation of the pump in response to the sensor signal.

20. A method, as claimed in claim 15, wherein the step of regulating includes the step of adjusting drug dosage and time interval for drug delivery.

21. A method of using one or more drugs to therapeutically treat a neural disorder over a predetermined time period by means of an implantable pump and a catheter having a proximal end coupled to said pump and a discharge portion for infusing therapeutic dosages of said one or more drugs, as well as a signal generator and an implantable electrode having a proximal end and a stimulation portion, the method comprising the steps of:

(a) surgically implanting the electrode so that the stimulation portion lies at least in direct communication with tissue elements of a pedunculopontine nucleus (PPN);

(b) surgically implanting said catheter so that the discharge portion lies adjacent a predetermined infusion site in a brain;

(c) operating the signal generator to stimulate the PPN; and (d) operating the pump to discharge a predetermined dosage of at least one drug through the discharge portion of the catheter into the predetermined infusion site.

* * * * *